United States Patent
Koo (12)

(10) Patent No.: US 6,248,728 B1
(45) Date of Patent: Jun. 19, 2001

(54) PHOSPHATIDYLCHOLINE COMPOSITIONS AND METHODS FOR LOWERING INTESTINAL ABSORPTION AND PLASMA LEVELS OF CHOLESTEROL

(75) Inventor: Sung I. Koo, Manhattan, KS (US)

(73) Assignee: Kansas State University Research Foundation, Manhatten, KS (US)

( * ) Notice: Subject to any disclaimer, the term of this patent is extended or adjusted under 35 U.S.C. 154(b) by 0 days.

(21) Appl. No.: 09/523,042

(22) Filed: Mar. 10, 2000

(51) Int. Cl.$^7$ .................................................. A61K 31/685
(52) U.S. Cl. ...................................................... 514/78
(58) Field of Search .................................................. 514/78

(56) References Cited

PUBLICATIONS

O'Connor et al, Chemical Abstracts, vol. 89, abstract No. 21085, 1978.*

Rodgers, J.B. et al., "The Effect of Synthetic Diether Phospholipid on Lipid Absorption in the Rat", *J. Lab. Clin. Med.*, vol. 89, No. 1, pp. 147–152, Jan. 1977.

Noh, Sang K. et al., "Estradiol Replacement in Ovariectomized Rats Increases the Hepatic Concentration and Biliary Secretion of α–Tocopherol and Polyunsaturated Fatty Acids", *J. Nutr. Biochem.*, vol. 10, pp. 110–117, Feb. 1999.

Ahn, Joungjwa et al., "Intraduodenal Phosphatidylcholine Infusion Restores the Lymphatic Absorption of Vitamin A and Oleic Acid in Zinc–deficient Rats", *J. Nutr. Biochem.*, vol. 6, pp. 605–612, Nov. 1995.

\* cited by examiner

*Primary Examiner*—William R. A. Jarvis
(74) *Attorney, Agent, or Firm*—Hovey, Williams, Timmons & Collins

(57) ABSTRACT

A method and composition for reducing the intestinal absorption of cholesterol in humans or animals are provided. Broadly, the methods comprise ingesting a composition (or a food product including the composition) comprising a substituted phosphatidylcholine compound, or comprising sufficient quantities of a phosphatidylcholine compound to provide from about 20–70% by weight of $C_{18}$ or higher alkyl groups. Preferred substituted phosphatidylcholine compounds include monoether phosphatidylcholines, diether phosphatidylcholines (wherein the alkyl group bonded to the second carbon atom of the glycerol moiety is a $C_{17}$ or higher alkyl group), or ester or diester phosphatidylcholines. Preferred $C_{18}$ or higher alkyl groups include $C_{18}$–$C_{22}$ alkyl groups, preferably bonded to the second carbon atom of the glycerol moiety of the phosphatidylcholine compound.

15 Claims, 3 Drawing Sheets

PHOSPHATIDYLCHOLINE COMPOSITIONS AND METHODS FOR LOWERING INTESTINAL ABSORPTION AND PLASMA LEVELS OF CHOLESTEROL

FEDERALLY SPONSORED RESEARCH/DEVELOPMENT PROGRAM

This invention was made with government support under Grant 96-35200-3207 awarded by the United States Department of Agriculture. The government has certain rights in the invention.

BACKGROUND OF THE INVENTION

1. Field of the Invention

The present invention is broadly concerned with methods and compositions for decreasing the intestinal absorption of cholesterol in humans and animals. More particularly, the inventive methods comprise administering by ingestion a quantity of a substituted ester or ether phosphatidylcholine compound, or a composition including one or more phosphatidylcholine compounds, with the composition having a particular $C_{18}$ alkyl group profile.

2 Description of the Prior Art

Cardiovascular disease is a leading cause of death in the United States, with a rather large number of people dying of cardiovascular disease by the age of 50. Atherosclerosis, which contributes to cardiovascular disease and stroke, can begin at a very early age. People with elevated serum cholesterol levels are more likely than their counterparts with normal cholesterol levels to have coronary heart disease.

Cholesterol is used by the body for the synthesis of the steroid hormones by certain endocrine glands and of bile acids by hepatocytes. Cholesterol is only found in animals, and is an essential constituent of cell membranes. Most dietary cholesterol is found in egg yolks and animal fat. Cholesterol that is taken up by the intestine is derived directly from the diet and via the biliary route. Free cholesterol is synthesized in the liver and secreted into the intestine via bile ducts. Cholesterol from the diet and bile are absorbed from the lumen of the small intestine by the intestinal epithelial cells, esterified, and incorporated intracellularly into chylomicrons and, in minor amounts, into very low density lipoproteins (VLDL), both of which are secreted into lymphatics that ultimately join the bloodstream. The chylomicrons and VLDL deliver their triacyglycerols and some of their cholesterol to cells in muscle and adipose tissue. The cholesterol-enriched chylomicron remnants and VLDL remnants (intermediate density lipoprotiens (IDL) and low density lipoproteins (LDL)) then deliver cholesterol back to the hepatocyte. The VLDL from intestinal and liver cells can be converted to LDL by hydrolysis of their triacylglycerols by lipoprotein lipase. LDL contain three-fourths of the total plasma cholesterol.

In hypercholesterolemia, the increase in the blood cholesterol level is associated mainly with a rise in LDL concentrations. However, the specific causes of hypercholesterolemia are complicated and varied. At least one kind of hypercholesterolemia is caused by a mutation in the gene for the LDL receptor that moves cholesterol out of the blood, primarily in the liver. Much more commonly, hypercholesterolemia has been associated with high dietary cholesterol, resulting in high cholesterol uptake from the intestine into the circulating blood. Reduction of hypercholesterolemia results in a delayed onset of atherosclerosis and a decrease in progression of atherosclerosis, thus reducing the risk of coronary heart disease. Specifically, there is evidence that relatively complicated plaques induced by hyperlipidemia will regress, and that further progression of atherosclerosis will cease when hyperlipidemia is removed. Therefore, efforts to prevent atherogenesis, to interrupt progression, and to promote regression of existing lesions by risk factor reduction are warranted.

Some forms of hyperlipidemia, including hypercholesterolemia, are potentially partially reversible with current techniques of preventive management. However, none of the current techniques is completely successful and many involve unwanted side effects and complications. Taking cholesterol-lowering drugs can result in a reduction in serum cholesterol. However, some drugs have serious side effects, including an increase in mortality through liver complications, or less severe side effects, such as constipation (cholestyramine), skin flushes, and muscle dysfunction. Dietary therapy is usually recommended for all patients with hypercholesterolemia but is not always effective.

Accordingly, there is a need for a method and composition which are effective in lowering intestinal absorption of cholesterol and which do not possess significant side effects.

SUMMARY OF THE INVENTION

The present invention overcomes these problems by broadly providing methods and compositions which decrease intestinal absorption of cholesterol. In more detail, the inventive methods comprise simply administering by ingestion a quantity of a compound according to the invention.

In one embodiment, the compound to be ingested is a monoether phosphatidylcholine, a diether phosphatidylcholine (wherein the alkyl group bonded to the second carbon atom of the glycerol moiety is a $C_{17}$ or higher alkyl group), or an ester or diester phosphatidylcholine. Preferred such compounds are depicted in Formula I.

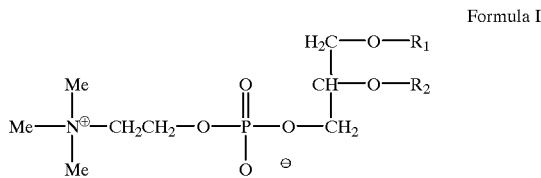

Formula I wherein:

(1) $R_1$ is selected from the group consisting of hydrogen, alkyl groups ($C_2$–$C_{24}$, and preferably $C_{12}$–$C_{20}$) and the group

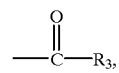

where $R_3$ is selected from the group consisting of hydrogen and alkyl groups ($C_1$–$C_{23}$, and preferably $C_{11}$–$C_{19}$);

(2) $R_2$ is selected from the group consisting of alkyl groups ($C_{10}$ or higher, preferably $C_{16}$ or higher, and more preferably from $C_{18}$–$C_{22}$) and

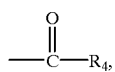

where $R_4$ comprises an alkyl group ($C_9$ or higher, preferably $C_{15}$ or higher, and more preferably from $C_{17}$–$C_{21}$); and (3) $R_1$ and $R_2$ are not both a $C_{17}$ or lower alkyl group.

In particularly preferred compounds of Formula I, $R_2$ comprises a $C_{18-22}$ alkyl group or the group

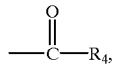

wherein $R_4$ comprises a $C_{17}$–$C_{21}$ alkyl group.

In another embodiment, the inventive compositions include a phosphatidylcholine compound comprising a $C_{18}$ or higher alkyl group, preferably bonded to the second carbon atom of the phosphatidylcholine gylcerol moiety. The composition preferably comprises from about 20–70% by weight, preferably from about 35–70% by weight, and more preferably from about 55–70% by weight of the $C_{18}$ or higher alkyl group(s), based upon the total weight of the composition taken as 100% by weight. Preferably, essentially all (i.e., at least about 95%, preferably at least about 98%, and more preferably at least about 99%) of the phosphatidylcholine compounds present in the composition are free of unsaturated carbon chains on the first and second carbon atoms of their respective glycerol moieties.

Regardless of the form of the inventive composition, it should be orally ingested (e.g., in a tablet form) within about 60 minutes (either prior to or after), and preferably within about 30 minutes, of the consumption of food or beverages containing cholesterol. Alternately, the composition can be mixed with (or pre-manufactured with) a food or beverage so that the composition is consumed simultaneous to consumption of the food or beverage. Examples of suitable food or beverages for supplementation with the inventive compositions include breads, cookies, cakes, candies, butter, milk, and margarine. In any case, the inventive composition should be consumed in sufficient quantities so that the weight ratio of ingested phosphatidylcholine compound to cholesterol ingested is at least about 2:1, preferably at least about 5:1, and more preferably from about 7:1 to about 30:1.

Consuming the compositions according to the invention will result in a decrease in intestinal cholesterol absorption of at least about 10%, preferably at least about 20%, and more preferably at least about 50% when compared to the intestinal cholesterol absorption without use of the inventive compositions.

DETAILED DESCRIPTION OF THE PREFERRED EMBODIMENTS

EXAMPLES

Figure 1:
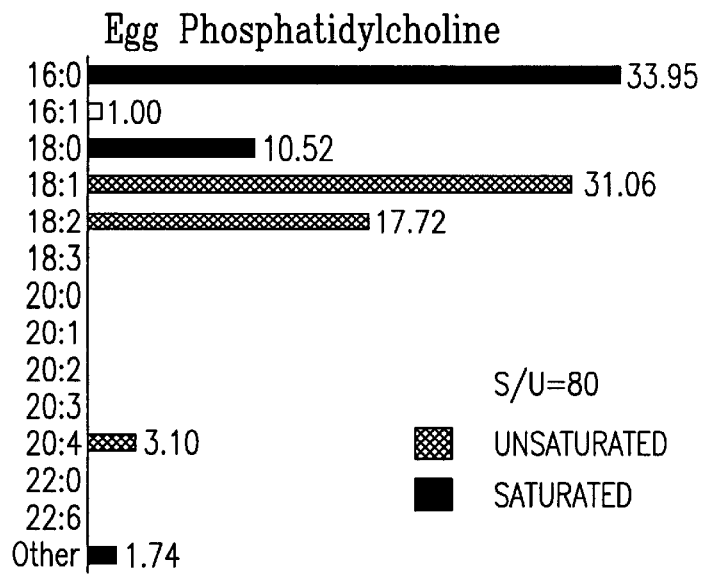
FIG. 1 is a graph depicting the saturated and unsaturated alkyl profile of a commercially available egg phosphatidylcholine.

The following examples set forth preferred methods in accordance with the invention. It is to be understood, however, that these examples are provided by way of illustration and nothing therein should be taken as a limitation upon the overall scope of the invention.

1. Animals and Diet

Thirty-two male Sprague-Dawley rats (obtained from Harlan Sprague Dawley, Inc., Indianapolis, Ind.) with respective initial body weights of 228.3±9.8 g were each individually placed in a plastic cage with stainless steel wire bottoms in a windowless room and subjected to a daily 12-hour light cycle followed by a 12-hour dark cycle with the light period being from 3:30 p.m. to 3:30 a.m. throughout the study. The temperature and humidity of the room were controlled at 22–25° C. and 30–50%, respectively. All rats were housed in an animal care facility fully accredited by the American Association for the Accreditation of Laboratory Animal Care.

Upon arrival, the rats were fed a nutritionally adequate diet containing soybean oil and egg whites in place of casein (see Table 1). The diet was formulated by Dyets, Inc. (Bethlehem, Pa.) according to the AIN-93 recommendations described by Reeves, et al., AIN-93 Purified Diets for Laboratory Rodents: Final Report of the American Institute of Nutrition Ad Hoc Writing Committee on the Reformulation of the AIN-76A Rodent Diet, J. Nutr. 123:1939–51 (1993). All rats were given free access to deionized water via a stainless steel watering system.

TABLE 1

| Composition of Diet | |
|---|---|
| INGREDIENT | g/kg |
| egg white | 200.0 |
| corn starch | 396.5 |
| dyetrose (dextrinized corn starch) | 132.0 |
| dextrose | 100.0 |
| cellulose | 50.0 |
| soybean oil[a] | 70.0 |
| mineral mix | 35.0 |
| vitamin mix | 10.0 |
| biotin (1 mg biotin per g of a sucrose mix) | 4.0 |
| choline bitartrate | 2.5 |

[a]contained 0.02% tert-butylhydroquinone, based upon the total weight of the soybean oil taken as 100% by weight.

2. Cannulation of the Mesenteric Lymph Duct

After 4–5 weeks of feeding, the rats were fasted for 16 hours, anesthetized with halothane, and the mesenteric lymph duct was cannulated as described by Noh et al., Estradiol Replacement in Ovariectomized Rats Increases the Hepatic Concentration and Biliary Secretion of α-tocopherol and Polyunsaturated Fatty Acids, J. Nutr. Biochem. 10:110–17 (1999). Basically, an abdominal incision was made along the midline by using a cauterizer. The major intestinal lymph duct was cannulated with polyethylene tubing (SV 0.31 tubing, inside diameter of 0.50 mm, outside diameter of 0.80 mm, obtained from Dural Plastics, Auburn, Australia).

An indwelling infusion catheter (Silastic medical grade tubing, inside diameter of 1.0 mm, outside diameter of 2.1 mm, obtained from Dow Corning, Midland, Mich.) was introduced into the upper duodenum via the gastric fundus and secured by a purse-string suture (4-0 Silk, Ethicon, Inc., Somerville, N.J.). After the abdominal incision was closed, the rats were placed in restraining cages in a heated chamber (30° C.) for 22–24 hours for post-operative recovery. During this recovery period, the rats were infused via the duodenal catheter with a maintenance solution consisting of 277 mM glucose, 144 mM NaCl, and 4 mM KCl/L at a rate of 3 ml/hr by using an infusion pump (Harvard Apparatus, Model 935, South Natick, Mass.).

3 Measurement of the Lymphatic Absorption of $^{14}$C-cholesterol

Figure 2:
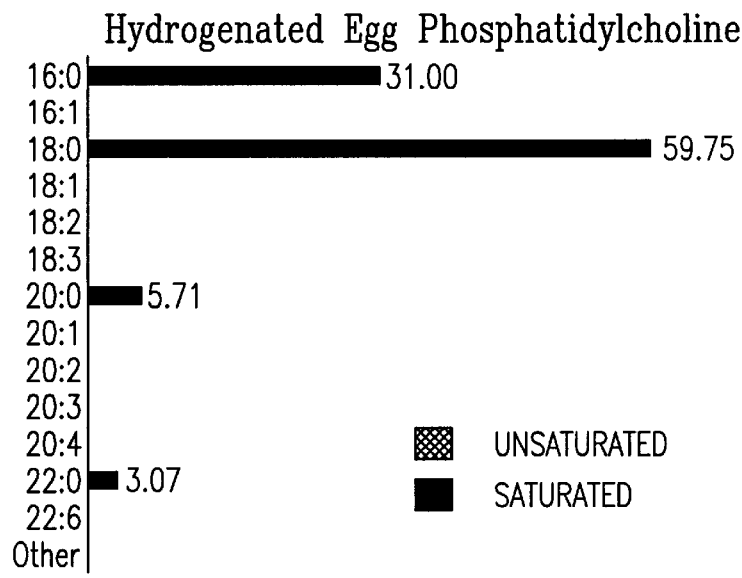
FIG. 2 is a graph depicting the saturated alkyl group profile of a commercially available hydrogenated egg phosphatidylcholine.
Figure 3:
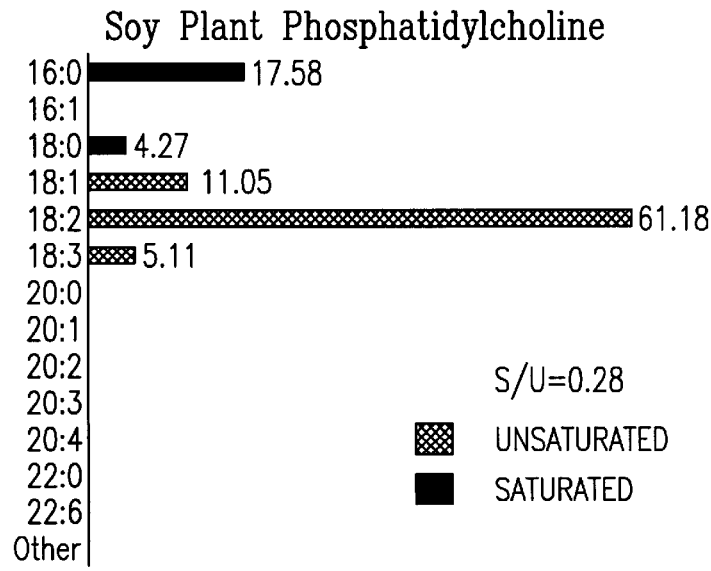
FIG. 3 is a graph depicting the saturated and unsaturated alkyl group profile of a commercially available soy plant phosphatidylcholine.

After post-operative recovery, each rat was infused with a lipid emulsion containing 5 μCi $^{14}$C-cholesterol (hereinafter referred to as "$^{14}$C—CH"; specific activity of 51.00 mCi/mmol, obtained from NEN Life Science Products, Inc., Boston, Mass.) at a rate of 3 ml/hr via the duodenal catheter under subdued light. The lipid emulsion consisted of 451.77 μmol triolein, 5 μCi $^{14}$C—CH, 20.69 μmol CH, 3.56 μmol α-tocopherol, and 396 μmol sodium taurocholate with 100 μmol of one of three types of phosphatidylcholito as "NPC") in 4 ml of phosphate-buffered saline (PBS —6.75 mM $Na_2HPO_4$, 16.5 mM $NaH_2PO_4$, 115 mM NaCl, 5 mM KCl, and pH of 6.63) as assigned to four groups of rats. The three types of PC included: soybean PC (hereinafter referred to as "SPC"; purity>99%; Avanti Polar Lipids, Inc., Alabaster, Ala.); egg yolk PC (hereinafter referred to as "EPC"; purity 99%; Avanti Polar Lipids, Inc.); and hydrogenated egg yolk PC (hereinafter referred to as "HPC"; purity>99%; Avanti Polar Lipids, Inc.). FIGS. 1–3 depict the alkyl group profile of the egg, hydrogenated egg, and soy plant phosphatidylcholine samples, respectively. In each of FIGS. 1–3, "16:0, " for example, refers to a $C_{16}$ alkyl group with no double bonds, while "16:1" refers to a $C_{16}$ alkyl group with 1 double bond.

Figure 4:
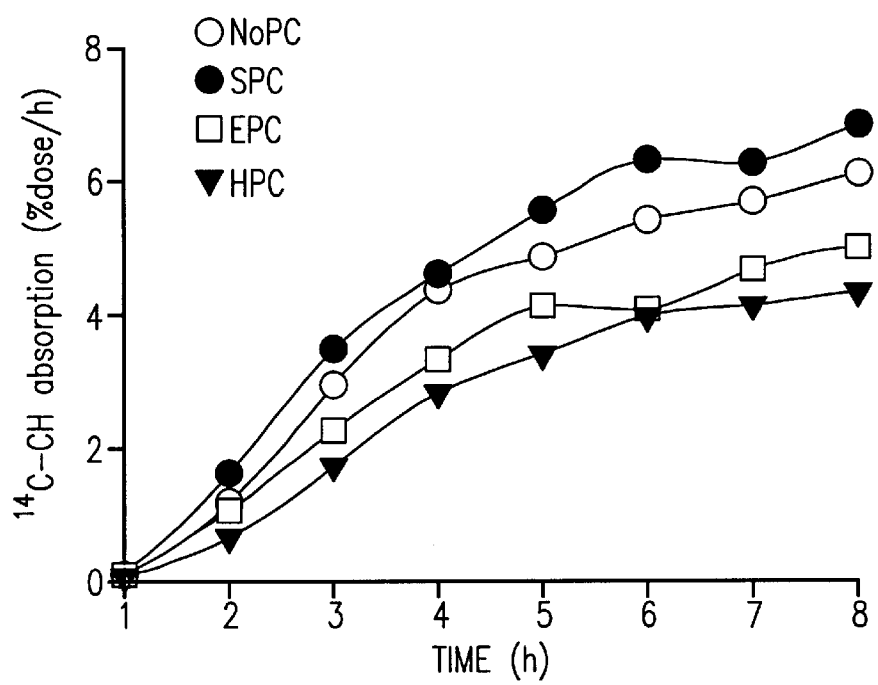
FIG. 4 is a graph comparing $^{14}$C—CH absorption after ingestion of egg phosphatidylcholine (EPC), hydrogenated egg phosphatidylcholine (HPC), or soy plant phosphatidylcholine (SPC) over time.
Figure 5:
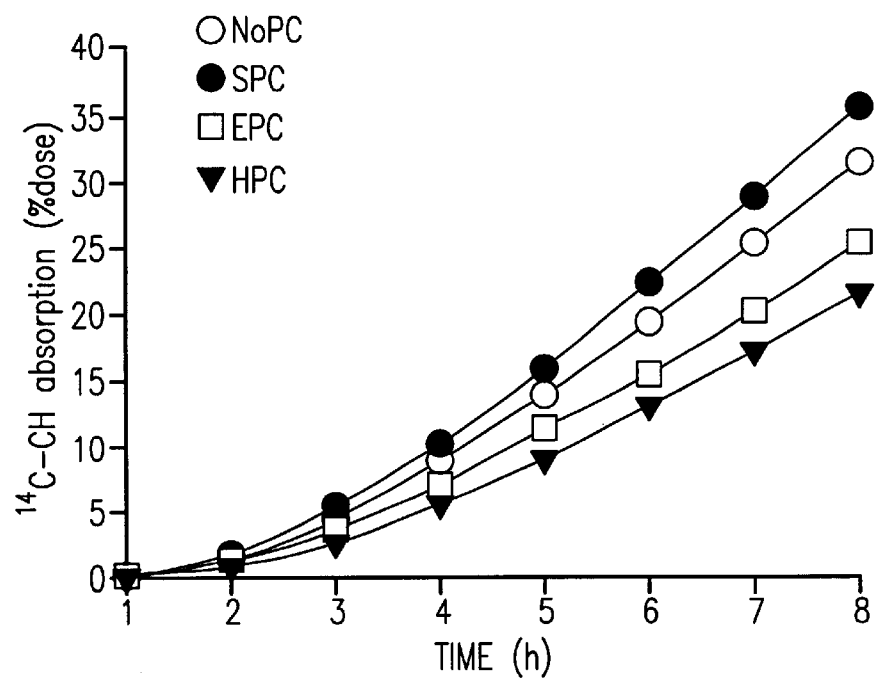
FIG. 5 is a graph comparing $^{14}$C—CH absorption after ingestion of egg phosphatidylcholine (EPC), hydrogenated egg phosphatidylcholine (HPC), or soy plant phosphatidylcholine (SPC) over time.

The lymph samples were collected hourly in pre-weighed, ice-cold centrifuge tubes containing 4 mg of $Na_2$-EDTA. The hourly lymph samples of 100 μl were mixed with a scintillation liquid (Scinti Verse, Fisher Scientific Company, Fair Lawn, N.J.) and counted to determine $^{14}$C radioactivity appearing in the lymph (Beckman LS-6500, Beckman Instruments, Fullerton, Calif.). All samples were ice-chilled and handled under subdued light. FIGS. 4 and 5 depict the $^{14}$C—CH absorption determined in these samples.

4. Determination of Lymphatic Output of Phospholipids

Figure 6:
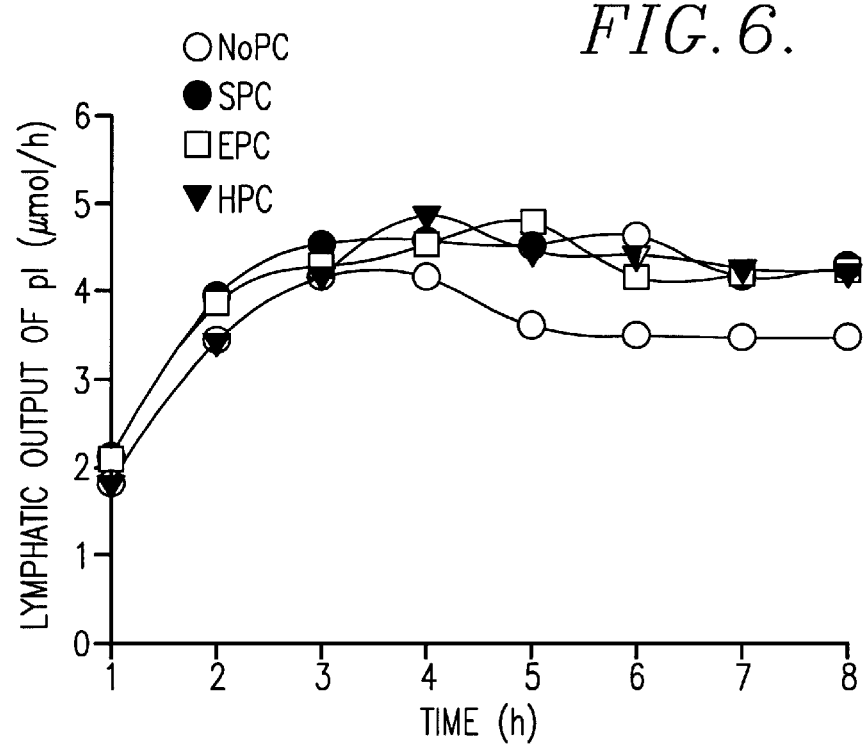
FIG. 6 is a graph comparing the lymphatic output of phospholipids after ingestion of egg phosphatidylcholine (EPC), hydrogenated egg phosphatidylcholine (HPC), or soy plant phosphatidylcholine (SPC) over time.
Figure 7:
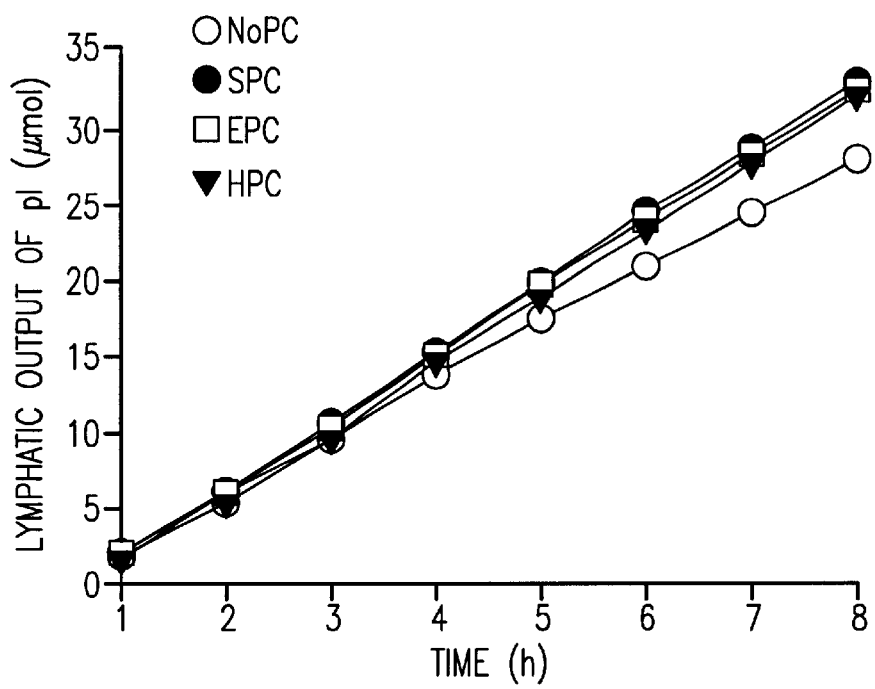
FIG. 7 is a graph comparing the lymphatic output of phospholipids after ingestion of egg phosphatidylcholine (EPC), hydrogenated egg phosphatidylcholine (HPC), or soy plant phosphatidylcholine (SPC) over time.

Lymph phospholipids (PL) were measured as described by Raheja et al. New Colorimetric Method for the Quantitative Estimation of Phospholipids Without Acid Digestion, J. Lipid Res. 14:695–97 (1973) except that the lipids were extracted from the 100 μl samples as described by Folch et al., A Simple Method for the Isolation and Purification of Total Lipids From Animal Tissues, J. Biol. Chem. 226:497–509 (1957) and dried under nitrogen. Next, 400 μl of chloroform was added to the dried lipid extract in a test tube followed by gentle vortexing for 5 seconds. To this mixture 100 μl of a chromogenic solution containing ammonium molybdate and mercury was added. The tube was tightly capped and placed in a boiling water bath for 1 minute followed by cooling to room temperature. Chloroform (4.0 ml) was added to the test tube, the tube was re-capped, and the mixture was vortexed gently for 2 seconds after which it was allowed to stand at room temperature for 30 minutes. The lower chloroform layer of the mixture was separated and used to determine the absorbance at 710 nm (UV-1201 Spectrophotometer, Shimadzu Scientific Instruments, Inc., Columbia, Md.). FIGS. 6 and 7 depict the lymphatic output of PL as determined in these tests.

5. Total Cholesterol Determination From Lymph

The total cholesterol (TC) was determined using O-phthaladehyde as described by Rudel et al., Determination of Cholesterol Using O-phthaladehyde, J. Lipid Res. 21:364–66 (1973). Basically, 300 μl of 33% KOH and 3 ml of ethanol were added to a test tube containing 100 μl of lymph after which the test tube was capped and mixed thoroughly. The capped tube was then placed in a 60° C. water bath for 15 minutes. The mixture was then cooled, and 5 ml of hexane was added to the tube followed by 1.5 ml of deionized water and thorough mixing.

The upper layer of lipid extracts was transferred to another test tube, and the solvent was evaporated in a 40° C. water bath under nitrogen. Next, 3 ml of O-phthaladehyde reagent (prepared by dissolving 50 mg of O-phthaladehyde in 100 ml of acetic acid) was added to the mixture, and the mixture was thoroughly mixed to dissolve all of the sample. About 10 minutes later, 1.5 ml of concentrated sulfuric acid were carefully added by allowing the sulfuric acid to run down the inside wall of the test tube followed by thorough mixing. The absorbance was 550 nm between 10 and 90 minutes after the addition of the concentrated sulfuric acid. A standard curve was made each time from a standard solution of 1 mg cholesterol palmitate per ml of chloroform. FIGS. 8 and 9 depict the lymphatic output of total cholesterol as determined in these tests.

6. Statistical Analyses

All statistical analyses were performed using PC SAS (SAS Institute, Cary, N.C.). The analysis of variance (ANOVA) was used to compare the means among groups. The correlation of coefficients were determined by linear regression analyses, and the level of significance was determined at $p<0.05$.

7. Summary of Results

Some of the results of the foregoing tests are set forth in Table 2. The lymphatic absorption of $^{14}$C—CH was markedly lowered by EPC (24.7±2.5% dose) than SPC (34.9±1.2% dose) and NPC (i.e., the control, 30.8±2.0% dose). In the HPC-infused group, the absorption of $^{14}$C—CH was lowered further to 21.1±1.4% dose. The total lymphatic output of CH was also reduced significantly by EPC (16.9±1.8 μmol/8 hours) and by HPC (15.3±0.7 μmol/8 hours), compared with SPC (19.6±1.1 μmol/8 hours) and NPC (20.7±1.2 μmol/8 hours). The lymphatic outputs of PL remained the same regardless of the source of PC (EPC —32.2±1.7 μmol/8 hours; HPC —31.9±1.6 μmol/8 hours; and SPC —32.9±1.8 μmol/8 hours).

TABLE 2

PC Effect on Cumulative $^{14}$C-CH Absorption, Lymphatic Outputs of Phospholipids, and Total Cholesterol
Lymphatic Lipids Output in 8 Hours

|  | Group 1 (NPC)[1, 2] | Group 2 (SPC)[1, 2] | Group 3 (EPC)[1, 2] | Group 4 (HPC)[1, 2] |
|---|---|---|---|---|
| $^{14}$C-CH absorption (% dose) | 30.75 ± 2.04[b] | 34.90 ± 1.19[a] | 24.60 ± 2.47[c] | 21.08 ± 1.42[d] |

TABLE 2-continued

PC Effect on Cumulative $^{14}$C-CH Absorption, Lymphatic Outputs of Phospholipids, and Total Cholesterol Lymphatic Lipids Output in 8 Hours

|  | Group 1 (NPC)[1,2] | Group 2 (SPC)[1,2] | Group 3 (EPC)[1,2] | Group 4 (HPC)[1,2] |
|---|---|---|---|---|
| Phospholipids ($\mu$mol) | 27.21 ± 1.30[b] | 32.88 ± 1.84[a] | 32.22 ± 1.71[a] | 31.79 ± 1.55[a] |
| Total Cholesterol ($\mu$mol) | 20.68 ± 1.21[a] | 19.57 ± 1.06[a] | 16.94 ± 1.80[b] | 15.29 ± 0.65[b] |

[1]Values given are mean ± standard deviation; n = 5.
[2]Values in the same row not sharing a common superscript are significantly different (P < 0.05).

EXAMPLE 2

Various phospholipid ether analogues of bis-alkanoyl-L-α-phosphatidylcholines such as those shown in Formula II, can be prepared from an O-alkylation reaction described by Williamson et al., J. Chem. Soc. 4:229 (1852).

Formula II

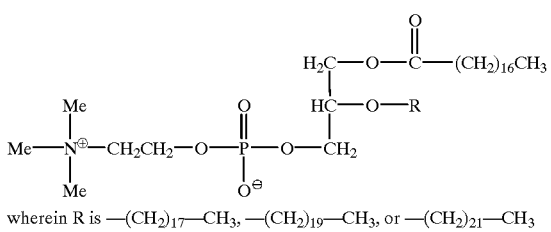

wherein R is —(CH$_2$)$_{17}$—CH$_3$, —(CH$_2$)$_{19}$—CH$_3$, or —(CH$_2$)$_{21}$—CH$_3$ Thus, the compounds of Formula II are prepared by treating the compound of Formula III with an alcohol and an alkyl triflate.

Formula III

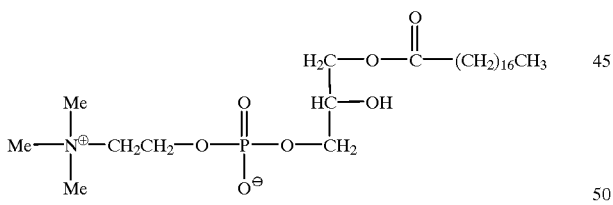

Scheme A below depicts the reactions which form each of the three possible compounds of Formula II.

Scheme A

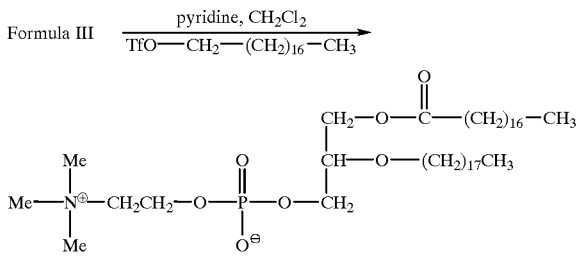

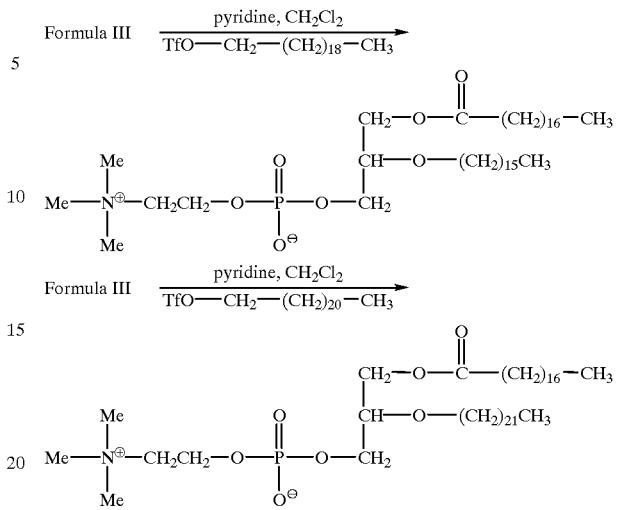

We claim:

1. A method of reducing absorption of cholesterol by the intestine, said method comprising the step of administering by ingestion a quantity of a composition comprising phosphatidylcholine compounds, each of said compounds individually having the formula

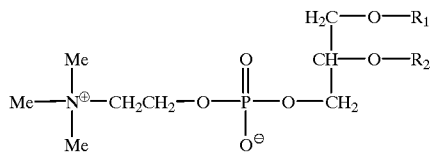

wherein:

(1) R$_1$ is selected from the group consisting of hydrogen, alkyl groups, and the group

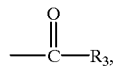

where R$_3$ is selected from the group consisting of hydrogen and alkyl groups;

(2) R$_2$ is selected from the group consisting of alkyl groups and the group

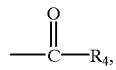

where R$_4$ comprises an alkyl group; and (3) said compound comprising at least one of

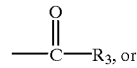

$$-\overset{O}{\underset{\|}{C}}-R_4,$$

wherein at least about 95% of the phosphatidylcholine compounds present in the composition are free of unsaturated carbon chains in their respective $R_1$ and $R_2$ groups.

2. The method of claim 1, wherein $R_2$ comprises a $C_{18}$–$C_{22}$ alkyl group.

3. The method of claim 1, wherein $R_2$ comprises the group $$-\overset{O}{\underset{\|}{C}}-R_4,$$

and $R_4$ comprises a $C_9$ or higher alkyl group.

4. The method of claim 3, wherein $R_4$ comprises a $C_{17}$–$C_{21}$ alkyl group.

5. The method of claim 1, wherein said compound is present in a food or beverage.

6. The method of claim 5, wherein said food or beverage is selected from the group consisting of breads, cookies, cakes, candies, butter, milk, and margarine.

7. The method of claim 1, wherein said compound is ingested within about 60 minutes of the ingestion of a food or beverage containing cholesterol.

8. The method of claim 7, wherein said compound-ingesting step results in at least about a 10% decrease in intestinal cholesterol absorption as compared to cholesterol absorption without said compound-ingesting step.

9. The method of claim 7, wherein said compound-ingesting step comprises ingesting sufficient quantities of said compound so that the weight ratio of ingested compound to cholesterol ingested with said food or beverage is at least about 2:1.

10. A food or beverage supplemented with a quantity of a composition comprising phosphatidylcholine compounds, each of said compounds individually having the formula $$\text{Me}-\overset{\text{Me}}{\underset{\text{Me}}{N^{\oplus}}}-CH_2CH_2-O-\overset{O}{\underset{O^{\ominus}}{\overset{\|}{P}}}-O-\overset{H_2C-O-R_1}{\underset{CH_2}{\overset{CH-O-R_2}{|}}}$$

wherein:

(1) $R_1$ is selected from the group consisting of hydrogen, alkyl groups, and the group $$-\overset{O}{\underset{\|}{C}}-R_3,$$

where $R_3$ is selected from the group consisting of hydrogen and alkyl groups;

(2) $R_2$ is selected from the group consisting of alkyl groups and the group $$-\overset{O}{\underset{\|}{C}}-R_4,$$

where $R_4$ comprises an alkyl group; and (3) said compound comprising at least one of $$-\overset{O}{\underset{\|}{C}}-R_3, \text{ or } -\overset{O}{\underset{\|}{C}}-R_4,$$

wherein at least about 95% of the phosphatidylcholine compounds present in the composition are free of unsaturated carbon chains in their respective $R_1$ and $R_2$ groups.

11. The food or beverage of claim 10, wherein $R_2$ comprises a $C_{18}$–$C_{22}$ alkyl group.

12. The food or beverage of claim 10, wherein $R_2$ comprises the group $$-\overset{O}{\underset{\|}{C}}-R_4,$$

and $R_4$ comprises a $C_9$ or higher alkyl group.

13. The food or beverage of claim 12, wherein $R_4$ comprises a $C_{17}$–$C_{21}$ alkyl group.

14. The food or beverage of claim 10, wherein said food or beverage is selected from the group consisting of breads, cookies, cakes, candies, butter, milk, and margarine.

15. The food or beverage of claim 10, wherein said food or beverage comprises sufficient quantities of said phosphatidylcholine compound so that the weight ratio of phosphatidylcholine compound to cholesterol present in said food or beverage is at least about 2:1.

* * * * *